United States Patent [19]

Ekbladh et al.

[11] Patent Number: 4,490,136
[45] Date of Patent: Dec. 25, 1984

[54] TROCAR

[75] Inventors: Fred V. G. Ekbladh, Särö; Hans Tillander, Göteborg, both of Sweden

[73] Assignee: Aktiebolaget Meteve, Goteborg, Sweden

[21] Appl. No.: 425,953

[22] Filed: Sep. 28, 1982

[30] Foreign Application Priority Data

Oct. 14, 1981 [SE] Sweden ................. 8106075

[51] Int. Cl.³ ............................. A61B 17/34
[52] U.S. Cl. .................... 604/22; 604/272; 128/339
[58] Field of Search .......... 128/305, 339; 604/22, 604/117, 272–274

[56] References Cited

U.S. PATENT DOCUMENTS 1,333,745  3/1920  Wescott ..................... 604/22 X
1,600,884  9/1926  Jones ......................... 128/339 X
3,115,138  12/1963 McElvenny et al. ......... 604/133
3,602,218  8/1971  Riordan et al. ............. 604/117 X
3,861,393  1/1975  Durand ....................... 604/274

FOREIGN PATENT DOCUMENTS 161460  3/1964  U.S.S.R. ...................... 604/272

Primary Examiner—Dalton L. Truluck
Attorney, Agent, or Firm—Brumbaugh, Graves, Donohue & Raymond

[57] ABSTRACT

A surgical trocar comprising a flattened oblong unit having at the front end an angled sharpened cutting edge, and at the rear end a device for removably attaching a tube for drainage or other purposes. The trocar's cutting edge produces fissure-shaped skin incisions which heal more easily than circular wounds, and the trocar's flattened shape reduces the risk of slippage and attendant damages to the patient and/or surgeon's hand from such slippage.

6 Claims, 7 Drawing Figures

TROCAR

TECHNICAL FIELD

The present invention relates to a new trocar.

The object of the present invention is to obtain a trocar by means of which a more safe penetration of tissue can be made without any risk for damages on patient and surgeon, as the surgeon can slip.

BACKGROUND ART

At operations but also very often in other circumstances there is a need for bringing a tubular means through the skin and/or other tissues. Thereby one uses to apply the tubular means on a strong, cylindrical, often somewhat bent needle and having this as an aid drawing the means through the tissues. Such a needle is called a trocar, and can often also be provided with a mandrel to facilitate a skin penetration. The point of the trocar is usually ground as a facet and very sharp, which is needed in order to be able to penetrate the actual tissues. However, the cylindrical trocars provide a bad hold to the hands provided with gloves often being dirty, and thus one often slips at the penetration, whereby, too often, the trocar slides along the fingers and thereby gives cut injuries on the surgeon's fingers. The cut injuries are often of serious character, and can mean a serious break in an intense surgery program, as is common at our hospitals. Sliding means a risk for penetration of other tissue of the patient than that tissue intended causing a delayed healing procedure, as well.

The trocar will give cylindrical wounds in the skin, as well, which wounds have showed to be more difficult to heal than other wounds, and are easily infected with a further discomfort to the patient as a consequence.

DESCRIPTION OF THE PRESENT INVENTION

It has now surprisingly been shown possible to be able to eliminate these drawbacks and to obtain a trocar which gives more easily healed wounds, and thereby a reduced risk for infections, but primarily the risk for slippage and uncontrollable cut injuries on the surgeon's hands is reduced. The present invention is thereby characterized by a substantially band shaped unit provided with a cutting edge in its one end and with a device to attach, preferably movably, a tubular means in its other end.

According to a preferred embodiment of the invention the edge provided point is arranged with an angle to the longitudinal axis of the trocar, whereby the point is ground to an edge to about two thirds of its length.

According to a further preferred embodiment of the invention the rear part of the trocar is provided with a rearwardly increasing enlargement.

According to another, further embodiment of the invention the trocar is bent.

BEST MODE OF CARRYING OUT THE INVENTION

In the following the invention will be more closely described with reference to the attached drawings, wherein FIG. 1 shows a preferred embodiment of the invention seen from above;

Figure 1:
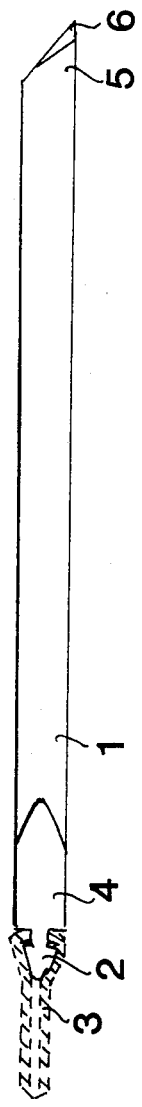
Figure 2:
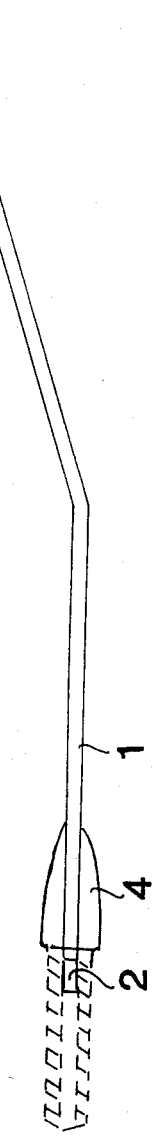
FIG. 2 shows the embodiment of FIG. 1 seen from the side.

1 denotes a flat, bandshaped, oblong unit suitably prepared in stainless steel. The length of the unit is about 15 cm and its width is half of the circumference of a tube, or tubular means, which is intended to be attached to the trocar, or usually about 1 cm. The thickness of the unit is one to some millimeters, and shall be enough to give a desired stiffness to the trocar. The thickness is thus dependent on the choice of material. The trocar 1 is further bent, substantially at the middle to an angle of about 20°. The trocar 1 is in its rear end provided with a hook 2 over which a tube 3 is intended to be brought and removably attached thereto. The hook 2 is an integrated part of the rear end of the trocar and is suitably punched out of its rear end. In the rear end of the trocar 1, immediately in front of the hook 2, an enlargement 4 is arranged. The enlargement 4 is decreasing in thickness in the direction towards the front end of the trocar. The object of the enlargement 4 is to widen the incision of a tissue to a diameter, which is the same as of a tube, which is to brought through the incision, and which is to be attached to the trocar 1. Besides the object of widening the incision of a tissue the object of the enlargement 4 is to protect the tube 3 from being drawn off the hook 2 and thereby involuntarily removed from the trocar 1. The enlargement 4 can be said to be drop-shaped with a flat thick-end. The trocar 1 is in its front end obliquely cut against its longitudinal axis to form tapered an oblique, asymmetric point 5. The point 5 is provided, by means of grinding, with a cutting edge 6. The edge 6 extends from the point and two thirds of the width of the trocar.

The hook 2 has a width which at least corresponds to half the circumference of the lumen of the tube. The hook 2 is further somewhat tapered in order to facilitate the attachment of the tube 3.

The enlargement 4 is suitably a casted-on unit either of metal or of plastic.

Figure 3:
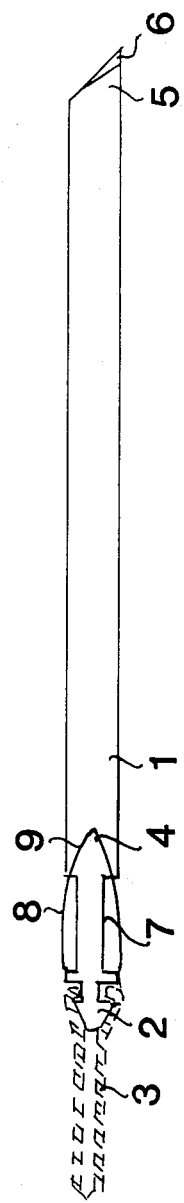
FIG. 3 shows another preferred embodiment of the invention seen from above.
Figure 4:
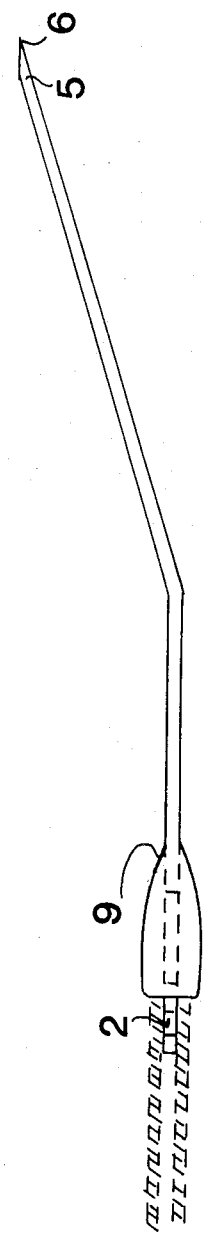
FIG. 4 shows the embodiment of FIG. 3 seen from the side.

In FIGS. 3 and 4 another preferred embodiment of the invention is shown, where the rear part of the trocar 1 is provided with a hook 2 and in front of this, a recess on each side, whereby the trocar 1 in this part has about half its width. The recesses are denoted 7. The enlargement 4 consists of an elastic unit 9 made out of a plastic material, which unit is provided with a matching-joint 8 going through, which unit is threaded onto the trocar 1 and snaps into the recesses 7.

In using the trocar 1 of the invention it has been found that lateral cutting effects are totally eliminated, whereby slipping and uncontrollable tissue penetration is avoided. Further the edge 6 shown enables the trocar 1 to split the skin in the fissure direction, whereby fissure shaped wounds are obtained which heal rapidly without any complicating infection.

Thus it has been found that the trocar 1 can be easily handled, penetrates without difficulty, and gives exact holes through the skin, which holds the tube, very often a drainage tube, perfectly in place. Further the trocar penetrates the skin in such a way that, when extracting the tube, no painful widening occurs.

Figure 5:
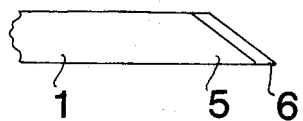
FIGS. 5 and 6 show different point and edge embodiments.
Figure 6:
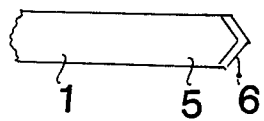

Although the point 5 and the edge 6 have been shown as an angled point with a ⅔ edge, the point can be designed with an edge all over its entire length. Further the front end can be designed with a more symmetrical shape with a ground faceted edge as shown in FIGS. 5 and 6.

Figure 7:
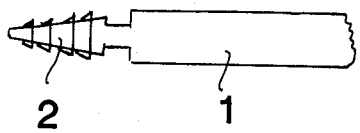
FIG. 7 shows another, further embodiment of the rear end of the trocar.

The hook 2 can further, as shown in FIG. 7, have a more extended shape with arranged counter-grips 10, which grip into the tube material and hold the tube 3 to the trocar 1 during the penetration.

Due to the simple technical shape of the trocar 1 it can be produced to a considerably lower price than other trocars having a cylindrical shape. Depending on the low price the trocar can be produced as a disposable trocar, whereby expensive running sterilizations are eliminated.

The trocar 1 can be used for any type of tube which needs to be brought through a tissue, such as catheters of different types, such as blood and urine catheters, or shunting tubes and stiff tubes for other tissue liquids. Further the trocar can be used for drainage tubes, which are used to drain an operation area after a surgical incision in order to facilitate and speed up healing.

The tube 3 can hereby be attached to the trocar immediately prior to the penetration, or be delivered as a set together with the trocar, in the latter case the tube suitably being forced upon the hook of the trocar by means of heat, and being removable by cutting the tube immediately after the trocar.

The above trocar has been shown in a bent embodiment, whereby the bend has been applied substantially at the middle of the trocar. Thus the bend can be carried out using another angle, greater or smaller, or be displaced so that the point become shorter or longer, or, in certain cases be completely eliminated, all depending on method or site of operation.

The material of the trocar has been said above to be stainless steel, but can of course be any other steel quality, which can be worked in the intended manner, e.g., to obtain a cutting edge. The trocar can further be made of a stiff plastic material, in the point of which a steel edge has been attached.

I claim:

1. An improved trocar for making a fissure-shaped incision in skin and bringing a tube through said skin and adjacent tissue with reduced risk of slippage in or cuts to the hands of a surgeon using said trocar, comprising:
    a flattened oblong unit having a front end provided with a front edge arranged at an angle to the longitudinal axis of the unit to form an oblique point, a rear end provided with means for attaching a tube thereto, and two substantially flat opposed elongate surfaces intermediate said ends to be grasped by said surgeon,
    said unit having a width equal to about one-half of the circumference of said tube, and
    said front edge provided with at least one facet that extends from said point rearwardly along said edge to form a sharpened cutting edge and enables said cutting edge to split said skin in the fissure direction,
    whereby use of said edge produces a fissure-shaped incision, and whereby the flattened shape of said unit enables the trocar to be used with reduced risk of slippage.

2. The trocar according to claim 1, wherein said oblong unit is bent substantially at the middle to a predetermined angle.

3. The trocar according to claim 2, wherein said predetermined angle is about twenty degrees.

4. The trocar according to claim 1 wherein said means includes an enlargement means that increases in thickness in a rearwardly direction for widening said incision in a lateral direction, thereby conforming the shape of incision substantially to that of the tube, and protecting the tube from involuntary removal during use of said trocar.

5. The trocar according to claim 4 wherein said facet extends rearwardly from said point along only about two-thirds of said front edge such that said sharpened cutting edge extends along only about two-thirds of said front edge.

6. The trocar according to claim 1 wherein said oblique point of said front edge is asymmetrically positioned far to one side of said flattened unit.

* * * * *

UNITED STATES PATENT AND TRADEMARK OFFICE
CERTIFICATE OF CORRECTION

PATENT NO. : 4,490,136

DATED : December 25, 1984

INVENTOR(S) : Ekbladh et al.

It is certified that error appears in the above-identified patent and that said Letters Patent is hereby corrected as shown below:

Column 1, line 47, "movably" should read --removably--;

Column 2, line 37, delete "tapered".

Signed and Sealed this

Twenty-eighth Day of May 1985

[SEAL]

Attest:

DONALD J. QUIGG

Attesting Officer     Acting Commissioner of Patents and Trademarks